(12) United States Patent
Melkonian et al.

(10) Patent No.: US 7,745,201 B2
(45) Date of Patent: Jun. 29, 2010

(54) METHOD AND DEVICE FOR CULTIVATING EUCARYOTIC MICROORGANISMS OR BLUE ALGAE, AND BIOSENSOR WITH CULTIVATED EUCARYOTIC MICROORGANISMS OR BLUE ALGAE

(75) Inventors: Michael Melkonian, Lohmar (DE); Bjoern Podola, Cologne (DE)

(73) Assignee: Algenion GmbH & Co. KG, Dietzenbach (DE)

( * ) Notice: Subject to any disclaimer, the term of this patent is extended or adjusted under 35 U.S.C. 154(b) by 634 days.

(21) Appl. No.: 10/565,537

(22) PCT Filed: Jul. 21, 2004

(86) PCT No.: PCT/EP2004/008144

§ 371 (c)(1),
(2), (4) Date: Jan. 19, 2006

(87) PCT Pub. No.: WO2005/010140

PCT Pub. Date: Feb. 3, 2005

(65) Prior Publication Data

US 2007/0010002 A1      Jan. 11, 2007

(30) Foreign Application Priority Data

Jul. 21, 2003    (EP) .................. 03016413

(51) Int. Cl.
*C12N 1/12*      (2006.01)
*C12M 1/00*      (2006.01)
*C12M 3/00*      (2006.01)

(52) U.S. Cl. ............... 435/257.1; 435/289.1; 435/293.1

(58) Field of Classification Search .............. None
See application file for complete search history.

(56) References Cited

U.S. PATENT DOCUMENTS

| | | | |
|---|---|---|---|
| 2,761,813 A | 9/1956 | Goetz | |
| 4,600,694 A | 7/1986 | Clyde | |
| 4,693,983 A * | 9/1987 | Davies et al. | ............... 435/41 |
| 4,937,196 A | 6/1990 | Wrasidlo et al. | |
| 5,445,473 A * | 8/1995 | Chaverot et al. | ............. 404/75 |
| 6,013,511 A | 1/2000 | Diels et al. | |

FOREIGN PATENT DOCUMENTS

| | | |
|---|---|---|
| AU | 199671316 | 6/1997 |
| EP | 0 112 155 | 6/1984 |
| EP | 0 239 272 | 9/1987 |
| GR | 1 003 266 | 1/1999 |
| RU | 2164893 C2 * | 2/1999 |
| WO | 90/02170 | 3/1990 |
| WO | WO 9002170 A1 * | 3/1990 |

OTHER PUBLICATIONS

D. Patankar and T. Oolman, "Wall-Growth Hollow-Fiber Reactor for Tissue Culture: II. A Theoretical Model," *Biotechnology & Bioengineering*, vol. 36, No. 1, Jun. 5, 1990, pp. 104-108.

Notification of Transmittal of Copies of Translation of the International Preliminary Report on Patentability dated Jun. 8, 2006, for corresponding International Application No. PCT/EP2004/008144 (8 pages).

* cited by examiner

*Primary Examiner*—Taeyoon Kim
(74) *Attorney, Agent, or Firm*—Shumaker & Sieffert, P.A.

(57) ABSTRACT

The invention relates to a method and device for cultivating eukaryotic microorganisms, whereby a perforated support (14) having a first major surface (19) and a second major surface (22) which is substantially impermeable to eukaryotic microorganisms (20), is prepared and the microorganisms (20) are applied on the first major surface (19). A layer, containing an aqueous solution (18), passes over the second major surface (22). The aqueous solution (18) moves from the second major surface (22) to the first major surface (19) substantially by means of capillary forces. As a result, the first major surface (19) is supplied the aqueous solution (18) and the applied microorganisms (20) grow on the first major surface (19).

13 Claims, 2 Drawing Sheets

Figure 1:
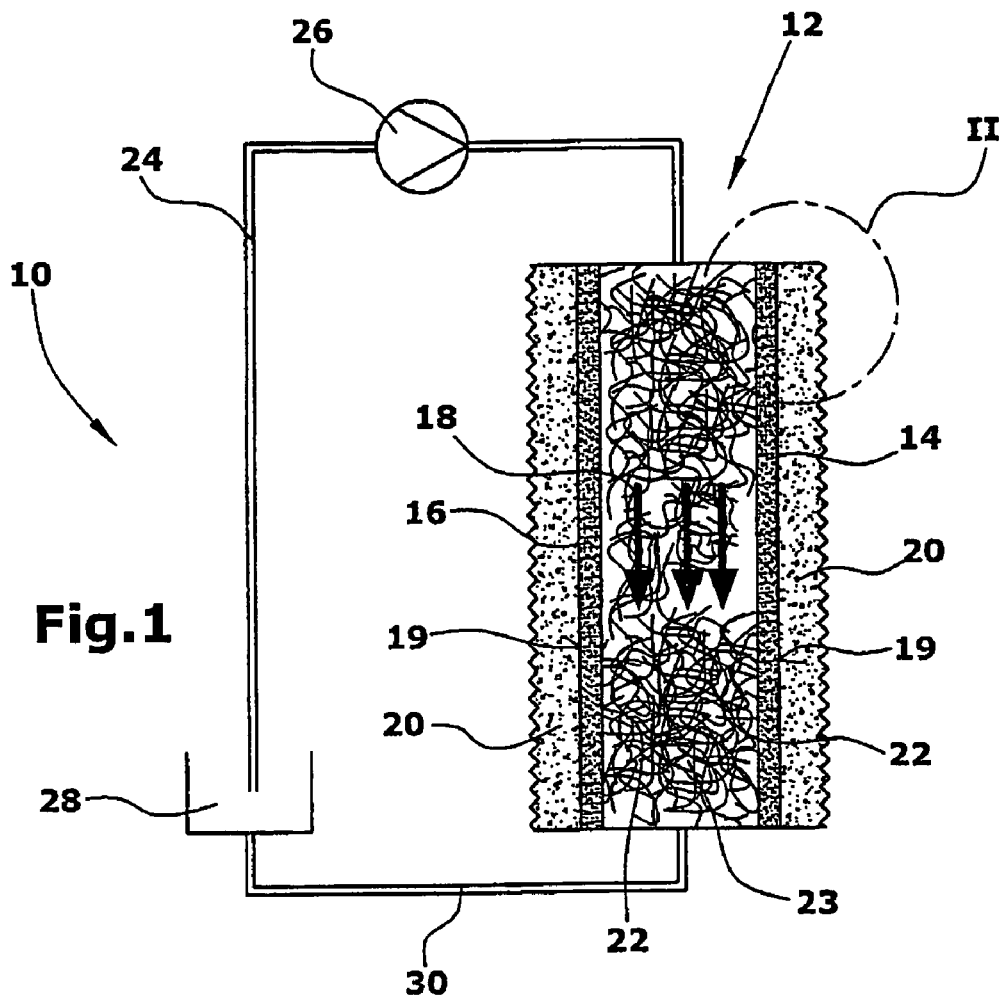

METHOD AND DEVICE FOR CULTIVATING EUCARYOTIC MICROORGANISMS OR BLUE ALGAE, AND BIOSENSOR WITH CULTIVATED EUCARYOTIC MICROORGANISMS OR BLUE ALGAE

The invention refers to a method and a device for cultivating eukaryotic microorganisms, and to a biosensor with cultivated eukaryotic microorganisms which may be, for example, algae and especially microalgae. The invention is also applicable to blue algae.

In contrast with prokaryotic microorganisms, eukaryotic microorganisms, especially algae, are used relatively infrequently in industrial plants for obtaining biomass with valuable ingredients.

Known methods for producing algae are cultivation in open basins, in tubular or plate-shaped photobioreactors. Disadvantages of these methods are the high costs for obtaining dry algae matter from the media suspension, unfavorable light conditions within the cultures, high costs caused by the additional use of $CO_2$, the elaborate harvesting of the cultivated algae, and the mechanical stress on the organisms caused by the circulation of the media and by the harvesting. Hitherto, no economic cultivation method for the industrial production of microalgae is known.

The cultivation of immobilized algae on thin layers described in WO 97/11154 can solve these problems. Here, algae are immobilized on a vertically arranged synthetic fiber tissue. A laminar flow of culture medium significantly accelerates the exchange of gas between the culture and the environment so that no additional supply of $CO_2$ is required. Further, the supply of light is more effective in thin layers. The biomass can be harvested with a comparatively small content of water so that the drying process is substantially more economic. Immobilizing reduces the mechanical stress, which is important when cultivating sensitive algae. This prior method shows problems mainly during the harvesting operation that causes heavy mechanical stress and resulting in an increased wear of the synthetic fiber substrate, thereby largely reducing the reusability thereof. Further disadvantages are the erosion of a part of the organisms from the substrate by the nutrient solution flowing above the same, and the contamination by microorganisms in the culture medium. The latter could be alleviated by a sterile culture medium supply system, which, however, would be elaborate.

EP-A-0 239 272 describes a plant for producing biomass, especially algae bio mass. Here, the cultivating is performed in a transparent tube around which a vertical core structure is wound.

From U.S. Pat. No. 2,761,813 and GR-B-1 003 266 it is known to drench a support for growing microorganisms with a nutrient solution into which the support is immersed or which is applied onto the support. Both systems require a bath operation that limits the efficiency of microorganism cultivation.

DHANANJAY PATANKAR ET AL.: "WALL-GROWTH HOLLOW-FIBER REACTOR FOR TISSUE CULTURE: ÖII. A THEORETICAL MODEL" BIOTECHNOLOGY AND BIOENGINEERING INCLUDING: SYMPOSIUM BIOTECHNOLOGY IN ENERGY PRODUCTION AND CONSERVATION; JOHN WILEY & SONS, New York, USA, Vol. 36, No. 1, Jun. 5, 1990 (1990-06-05), pages 104-108, XP000128553, ISSN: 0006-3592 describes a hollow fiber reactor for tissue cultures, wherein a nutrient solution flows through hollow fibers and reaches the outer side through the hollow fiber wall where the tissue cells are located. Removing these cells from the outer side is complex due to the cylindrical shape of the hollow fibers.

A system of tubes through which a nutrient solution can flow and at whose membrane walls microorganisms grow is described in WO-A-90/02170.

EP-A-0 112 155 describes a dynamically operating device, wherein two fluids flow in opposite directions through two respective adjacent channels separated by a membrane, on fluid comprising tissue cells and the other being a nutrient solution.

Further, U.S. Pat. No. 4,937,196 describes a membrane bioreactor wherein cell cultures are provided between adjacent membranes through which diffuse a nutrient solution on the one hand and extra cellular products as well as metabolic residues on the other hand.

U.S. Pat. No. 6,013,511 describes a system for extracting dissolved metals from waste water. The waste water flows along or on a membrane with immobilized microorganisms. From the side averted from the waste water flow, the microorganisms are fed a nutrient solution. Removing the microorganisms entails significant technological efforts.

Finally, U.S. Pat. No. 4,600,694 shows a device for harvesting microorganisms by scraping the same from rotating discs.

The technical problem underlying the invention is the improvement of a method for cultivating eukaryotic microorganisms as well as the provision of a device allowing for an improved method for cultivating eukaryotic microorganisms.

This problem is solved with a method having the features of claim 1 and a device according to claim 8 which, in one embodiment, can be employed as a biosensor according to claim 12.

The present method for cultivating eukaryotic microorganisms comprises the following steps:

a perforated support comprising a first major surface and a second major surface is provided, wherein the support comprises a web material and is essentially impermeable to eukaryotic microorganisms or to blue algae, the eukaryotic microorganisms or the blue algae are applied to the first major surface where they remain immobilized and from which they are adapted to be removed, an aqueous solution flows along the first major surface, a portion of the flowing aqueous solution is essentially transported by capillary forces from the second major surface through the support to the first major surface, whereby the first major surface is supplied with aqueous solution, and wherein the applied eukaryotic microorganisms or blue algae grow on the first major surface.

The novel cultivation system for microalgae, in particular, or other eukaryotic microorganisms or for blue algae, which represents the present invention, is based on the functional and structural division of a series of layers composed of at least two layers into a support layer on which the algae cultures are situated and a supply layer for feeding culture medium through the support layer.

Here, the supply layer is located on the one major surface of the support layer as a liquid film containing an aqueous solution and flowing along the support layer, whereas the microorganisms to be cultivated are situated on the other major surface of the support layer. The support layer (hereinafter also referred to as support) is made of web material, i.e. it is sheet-shaped. It is possible that the support layer is stationary and the aqueous solution flows along one of its major surfaces or that the support layer is moved along the aqueous solution.

One advantage of spatially separating the liquid film from the algae to be cultivated is, among other reasons, that now (small) algae can no longer be washed away from the support layer by the liquid. The perforated support layer further acts like a filter that allows liquid to pass to the algae, but, due to the miniature perforation, preventing microorganisms to get through the support layer from one major surface to the other major surface thereof. Thus, the risk of contamination is also reduced. Eventually, the cultivated microorganisms can be harvested in a simple manner by being removed from that major surface of the support layer on which they are cultivated without having to interfere with the structure of the system. At most, the supply of the aqueous solution has to be interrupted for the duration of the harvest.

The second major surface can be supplied with the aqueous solution, which preferably is a nutrient solution for cultivating the eukaryotic microorganisms, in different manners, it being possible, for example, to arrange the support layer in a vertically suspended manner and to supply the aqueous solution to one major surface at the top end of the support layer, the solution flowing down along this major surface because of gravity.

Alternatively, as is known per se from surface treatment systems for technical applications (e.g. layer coating methods for magnetic tapes, for example), it is possible to move the support layer over an open bath or basin, where only the major surface of the support layer to be wetted with the aqueous solution is contacted with the aqueous solution; the side of the support layer averted from the bath and provided with microorganisms makes no direct contact with the bath.

Another technical layer coating process that is also applicable in the context of the invention, provides that the aqueous solution exits from the top of an inclined plane through a slot nozzle or a plurality of single nozzles, flowing thereon to the lowermost edge to contact the support layer moved along the edge of the inclined plane and to be "taken along" thereby. Here, laminarily flowing multi-layered aqueous solutions could be used and reach the support layer over the inclined plane.

Finally, it is also possible to make the aqueous solution contact the respective major surface of the support layer in the form of a "liquid curtain".

Preferably, the aqueous solution is a nutrient solution for microorganisms.

In a particular embodiment of the present method, the perforated support is arranged on a distributing layer which when at least partly wetted or supplied with the aqueous solution distributes the same both over its thickness and its width and length, thus also distributing it over the support layer. Another perforated support may be arranged especially on the distributing layer.

In particular, the perforated web or sheet-shaped support used in the present method, the other perforated support and/or the distributing layer are hydrophilic.

When the support layer, the distributing layer and the supply layer are oriented vertically, the distributing layer may serve to removably retain the support layer that adheres to the distributing layer because of the liquid film adhesion.

The use of this material significantly facilitates the harvesting and reduces the costs thereof, while simultaneously imposing very little stress on the material. When a two-layered system uses a support layer permeable only to the culture medium, the passage of the eukaryotic microorganisms, especially of the algae, into the culture media flow is prevented. Thus, a washing out of the organisms is prevented on the one hand, resulting in an increased biomass productivity. On the other hand, costly operations to purify the culture medium can be omitted. Moreover, when a substrate layer impermeable to microorganisms is used, contamination risks to the algae cultures can be reduced.

The perforated support, the other perforated support and/or the distributing layer are made of organic or inorganic material, in particular.

The perforated support, the other perforated support and/or the distributing layer may especially be configured from mineral fibers, hydrophilic organic fibers or combinations thereof.

Suitable organic materials are, for example, paper, cellulose ester, in particular cellulose acetate, mixed cellulose ester, cellulose, cellulose nitrate, polyamides, polyesters and/or polyolefines.

The inorganic material may be, for example, a porous ceramic material and/or glass fiber.

According to the invention, after cultivation, the microorganisms can be loosened from the perforated support and/or from the other perforated support by the effect of mechanical forces such as scraping or by chemical treatment such as a treatment with surfactants and/or organic solvents.

In another embodiment, the microorganisms can be harvested together with the perforated support. This may be practical if the microorganisms are decomposed remaining on the support so as to obtain ingredients by extraction, for example. The extracted microorganisms or cellular debris can be separated mechanically from the extract together with the support.

In another embodiment, the microorganisms may be obtained by collecting loosened biomass in flowing culture medium.

In particular, the microorganisms can be loosened from the porous support after drying and may then be collected.

The present invention is particularly suited for algae and microalgae. However, the invention is also applicable to the cultivation of blue algae.

Under device aspects, the invention can be seen in the double-layered structure comprising the support and a film of an aqueous solution provided thereon. The present device for the cultivation of eukaryotic microorganisms, especially algae, thus comprises a perforated support comprising a first major surface and a second major surface opposite said first major surface, wherein the eukaryotic microorganisms or the blue algae are adapted to be cultivated on the first major surface of the perforated support, and the perforated support is essentially impermeable to the eukaryotic microorganisms or the blue algae to be cultivated, and a film comprising an aqueous solution, said film merely being in contact with the second major surface of the support and flowing along the second major surfaces, wherein the aqueous solution is adapted to be transported by capillary forces from the second major surface through the perforated support to the first major surface.

As a complement to a two-layered structure, it is also possible to chose a three-layered structure. This structure is characterized by two support layers, between which the liquid film is arranged in contact with the major surfaces of the supports facing each other.

For the aqueous solution to distribute evenly over the second major surface of the support layer, an advantageous development of the invention is provided with a (liquid) distributing layer exposed to the film of aqueous solution and, in particular, "drenched" thereby. The distributing layer preferably is a layer generating capillary forces transverse to the thickness of the support layer, the distributing layer being configured especially as a non-woven preferably of synthetic fibers (e.g. so-called geotextile). The second major surface of the support layer or each support layer is in contact with the distributing layer.

Moreover, the present device can be combined with the features of the previously described variants of the present method.

Besides the use as a device for the cultivation of eukaryotic microorganisms, the present two or three-layered structure may also be employed as a biosensor with eukaryotic microorganisms. According to the invention, this biosensor is provided with:

a perforated support comprising a first major surface and a second major surface opposite said first major surface, wherein the eukaryotic microorganisms or the blue algae are adapted to be immobilizedly cultivated on the first major surface of the perforated support, and the perforated support is essentially impermeable to the eukaryotic microorganisms or the blue algae to be cultivated, and a film comprising an aqueous solution which is merely in contact with the second major surface of the support and flows across said second major surface, wherein the aqueous solution is adapted to be transported by capillary forces from the second major surface through the perforated support to the first major surface, and wherein the cultivation takes place in dependence on the composition of the aqueous solution and/or a fluid being in contact with the first major surface of the perforated support and/or the eukaryotic microorganisms or the blue algae.

The microorganisms cultivatable on one of both major surfaces of the support are exposed to the environment. Growth or degradation occurs in response to the composition of the aqueous solution and/or the gas coming in contact with the microorganisms. Thus it is possible, for example, to check the aqueous solution or, more generally, an aqueous solution flow for certain ingredient matters. For example, it could be determined from the growth of certain microorganisms on the support that the aqueous solution flowing along the rear side contains certain ingredients. Similarly, it is also possible to perform this detection for the environmental gas in contact with the microorganisms.

Single embodiments of the present biosensor may have the same features as the present device. As such, advantageous developments of both the present device and the present biosensor form the subject matter of the individual dependent claims of the set of claims.

Figure 2:
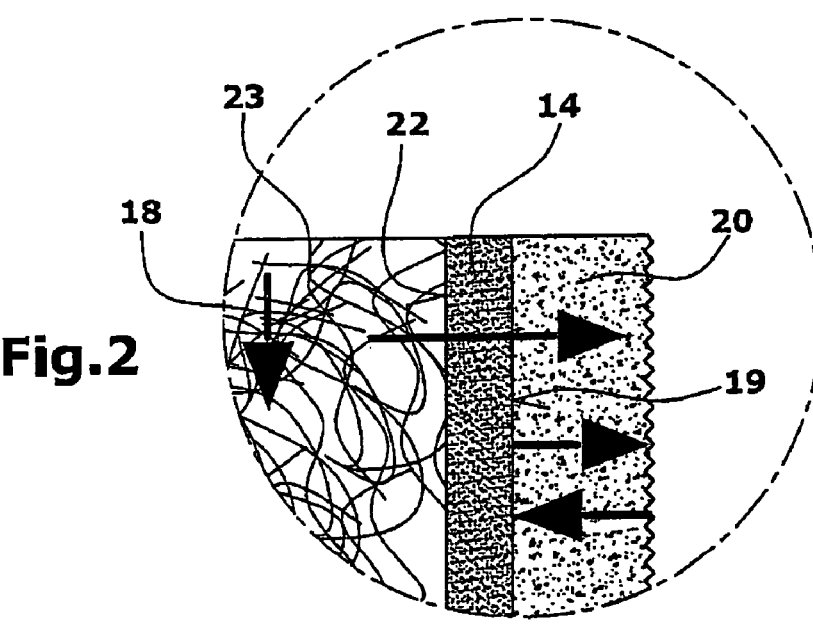
Figure 3:
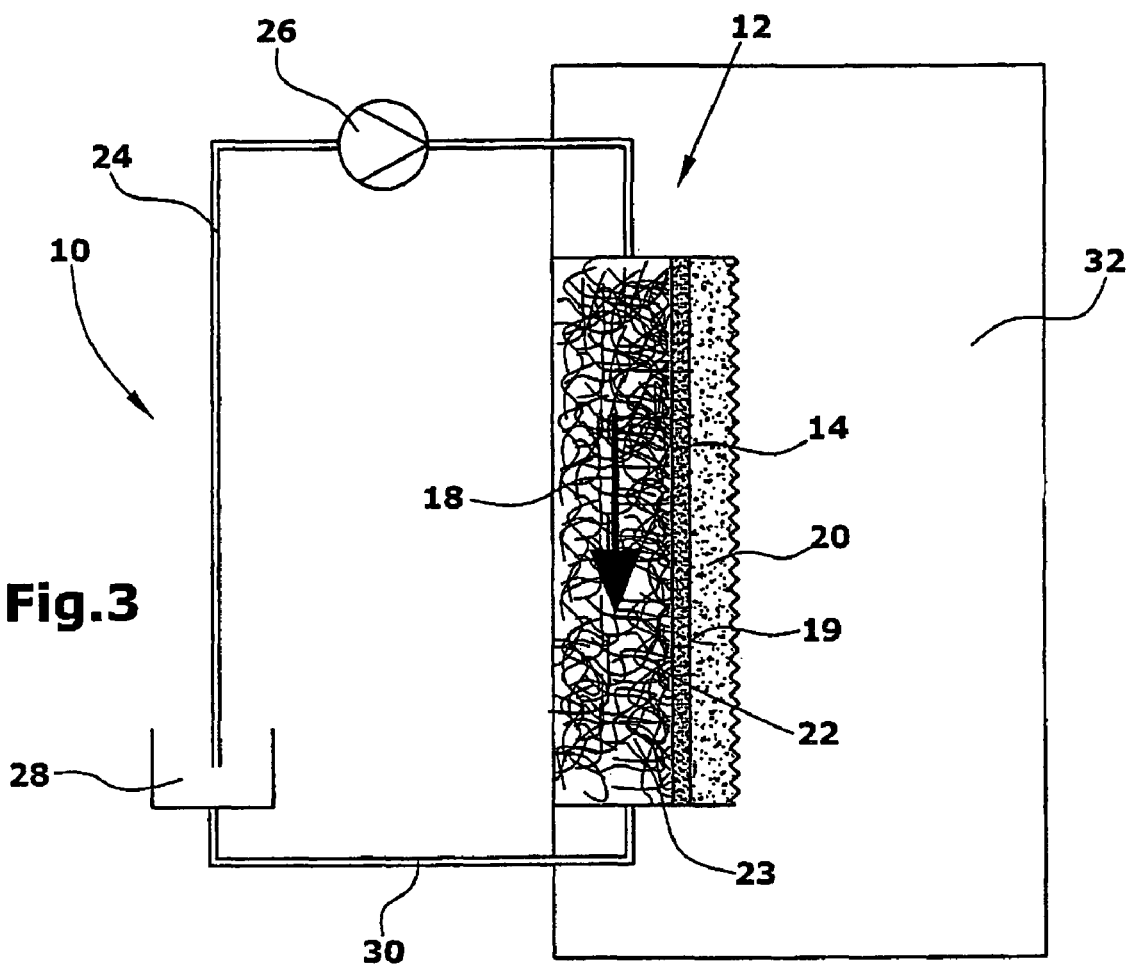
Figure 4:
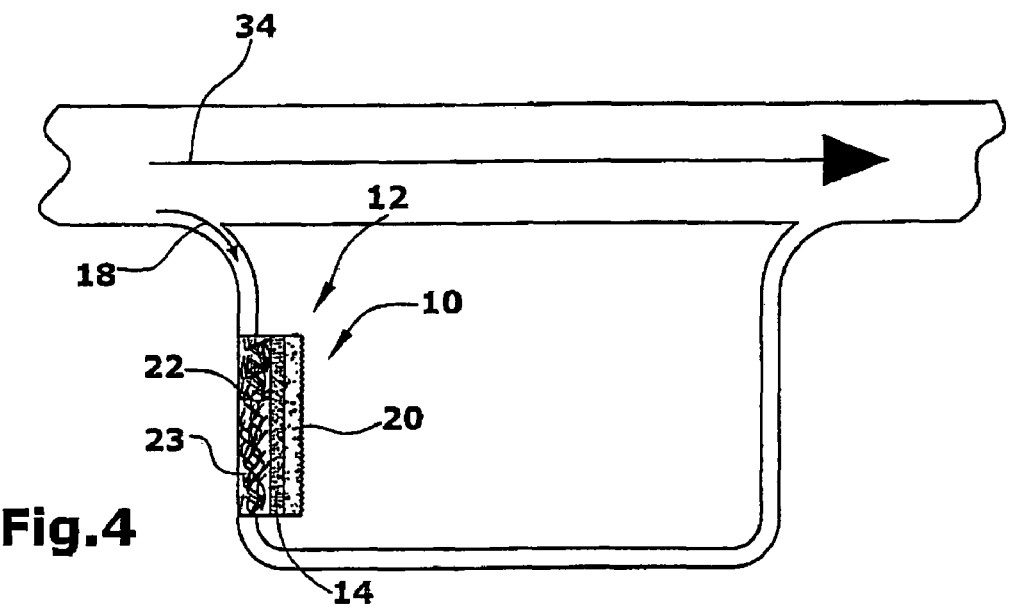

The following is a detailed description of the invention. Specifically, the Figures show:

FIG. 1 a schematic illustration of the cultivation method for algae on composite layers of selective permeability, FIG. 2 an upscaled detail of the composite layer arrangement of FIG. 1, FIG. 3 the arrangement of the composite layers for use as a biosensor for gases, and FIG. 4 the arrangement of the composite layers as an implementation of the biosensor for liquids.

FIG. 1 illustrates the general structure of the present device 10 for cultivating eukaryotic microorganisms, especially algae and microalgae. This Figure and the upscaled detail in FIG. 2 also illustrate the present method.

A composite layer system 12, arranged vertically in this embodiment, comprises two support layers 14, 16 between which an aqueous solution 18 flows along. The two support layers 14 are arranged in parallel to each other and are provided with eukaryotic microorganisms 20 on the averted outer first major surfaces 19. The flow of aqueous solution 18 (hereinafter referred to as liquid film) is in contact with the facing inner second major surfaces 22 of the two support layers 14. By means of the aqueous solution, a distributing layer 23 is fed through which the solution can anisotropically flow in the direction of its thickness and its width, the layer also being arranged between the two support layers 14 and 16. In this embodiment, the distributing layer 23 is configured as a non-woven of synthetic fibers. It provides for the distribution of the aqueous solution over the second major surfaces 22 of the support layers 14, 16.

The supply of aqueous solution to the composite layer system 12 is effected via a supply line 24 through which a pump 26 pumps aqueous solution from a reservoir 28. The portion of the aqueous solution 18 flowing from the composite layer system 12 reaches the reservoir 28 via a drain line 30 so that on the whole a circulation of the aqueous solution is established. However, this is not ultimately necessary for the invention. Other line systems may be used instead of feed and drain line systems.

The two support layers 14 are configured as membrane filters of mixed cellulose ester, for example, which are perforated accordingly. Due to this perforation, it is possible that capillary force effects let the aqueous solution 18 get from the second major surfaces 22 through the support layers 14 to the first major surfaces 19 thereof where it serves to feed the microorganisms 20. Thus, the aqueous solution 18 is a nutrient solution for the microorganisms 20.

Due to the filtering effect of the support layers 14, no microorganisms to be cultivated will get into the nutrient solution (aqueous solution 18). All microorganisms to be cultivated thus remain on the first major surface 19 of a support layer 14.

Further, the support layer 14 also acts as a separator between the nutrient flow and the site of cultivation of the microorganisms. This is advantageous in that no microorganisms can be "swept along" with the nutrient flow.

The above described filtering effect moreover prevents contamination of the microorganisms 20 through the nutrient solution or the flow thereof. For example, this significantly reduces the risk of growth and expansion of fungi or amoebae or other contaminating organisms that could cause the complete destruction of the microorganisms 20 to be cultivated.

The present device and the present method have been described above with reference to FIGS. 1 and 2 for the case where two perforated support layers facing each other and being provided with microorganisms are "fed" directly through a liquid film (aqueous solution 18). However, it is also conceivable that the liquid film only flows along the rear side of a support having the microorganisms to be cultivated provided on its front side.

FIGS. 3 and 4 illustrate two alternative arrangements for the use of the device of FIGS. 1 and 2 (in two-layered structure) as a biosensor. According to FIG. 3, the device 10 is arranged in a measuring space 32 to which the first major surface 19 of the composite layer system 12 bearing the microorganisms 20 is exposed. The supply of aqueous solution 18 (nutrient solution) to the composite layer system 12 is performed as explained with reference to the example in FIG. 1.

The growth behavior of the microorganisms 20 changes depending on the composition of the fluid (gas or liquid) present in the measuring space 32. By providing different or even the same microorganisms on the major surface 19 of the support layer 14, conclusions on the composition of the fluid can be derived from their growth behavior.

Finally, FIG. 4 illustrates the case in which the composition of the aqueous solution 18 can be sensed by means of the composite layer system 12. For example, it is thus possible to sense the flow 34 of a liquid to be measured. The aqueous solution 18 flowing along the rear side (major surface 22) of the support layer 14 as the aqueous solution 18 is branched from this liquid 34 and returned again further downstream. The growth of the microorganisms 20 will again allow to conclude on the composition of the liquid 34 to be examined. Here, it is also possible to arrange different microorganisms on the support layer 14.

The invention claimed is:

1. A method for cultivating eukuryotic microorganisms or blue algae, the method comprising:
    applying the eukaryotic microorganisms or blue algae to a first major surface of a sheet-shaped perforated support, wherein the sheet-shaped perforated support is essentially impermeable to the eukaryotic microorganisms or blue algae and wherein the eukaryotic microorganisms or blue algae remain immobilized on the first major surface and are adapted to be removed;
    supplying an aqueous solution to a second major surface of the sheet-shaped perforated support, wherein the aqueous solution flows along the second major surface of the sheet-shaped perforated support and wherein a portion of the aqueous solution flowing along the second major surface of the sheet-shaped perforated substrate is essentially transported by capillary forces from the second major surface to the first major surface through the sheet-shaped perforated support; and
    growing the eukaryotic microorganisms or blue algae on the first major surface of the sheet-shaped perforated support.

2. The method of claim 1, wherein a layer produced by the aqueous solution contains a distributing layer that distributes the aqueous solution across the second major surface.

3. The method of claim 2, wherein the distributing layer comprises a non-woven material, wherein the non-woven material is glass or plastic fibers.

4. The method of claim 3, wherein the distributing layer comprises a geotextile.

5. The method of claim 2, wherein the distributing layer is hydrophilic.

6. The method of claim 2, wherein the sheet-shaped perforated support and the distributing layer are hydrophilic.

7. The method of claim 1, wherein the sheet-shaped perforated support is hydrophilic.

8. The method of claim 2, wherein the distributing layer comprises one or more materials selected from the group consisting of mineral fibers and hydrophilic organic fibers.

9. The method of claim 2, wherein the distributing layer and the sheet-shaped perforated support comprise one or more materials selected from the group consisting of mineral fibers and hydrophilic organic fibers.

10. The method of claim 1, wherein the sheet-shaped perforated support comprises one or more materials selected from the group consisting of mineral fibers and hydrophilic organic fibers.

11. The method of claim 1, wherein the sheet-shaped perforated support comprises a first sheet-shaped perforated support, the method further comprising:
    supplying the aqueous solution between the second major surface of the first sheet-shaped perforated support and a second major surface of a second sheet-shaped perforated support, wherein the first and second sheet-shaped perforated supports have their second major surfaces facing each other and arranged essentially in parallel to each other.

12. The method of claim 1, further comprising:
    removing the eukaryotic microorganisms or the blue algae from the sheet-shaped perforated support by application of mechanical forces.

13. The method of claim 1, further comprising:
    removing the eukaryotic microorganisms or the blue algae from the sheet-shaped perforated support by application of chemical treatment.

\* \* \* \* \*